United States Patent [19]

Marinoff

[11] 4,180,075
[45] Dec. 25, 1979

[54] OPHTHALMOLOGICAL SURGICAL INSTRUMENT

[76] Inventor: Gerald P. Marinoff, 8 Rockford Dr., West Nyack, N.Y. 10994

[21] Appl. No.: 784,682

[22] Filed: Apr. 5, 1977

[51] Int. Cl.² ............................................. A61B 17/32
[52] U.S. Cl. ..................................... 128/305; 128/745
[58] Field of Search .............. 128/2 T, 305, 354, 2 B; 33/19 B, 21 B, 26, 174 D; 30/164.9, 293, 310; 83/821; 99/588; 3/13

[56] References Cited

U.S. PATENT DOCUMENTS

| | | | |
|---|---|---|---|
| 1,182,629 | 5/1916 | Birnbaum | 30/113.3 |
| 2,249,906 | 7/1941 | Longovia | 128/305 |
| 2,401,548 | 6/1946 | Chapman | 128/310 |
| 2,480,737 | 8/1949 | Jayle | 128/305 |
| 2,854,076 | 9/1958 | Keim | 30/310 |

Primary Examiner—Dalton L. Truluck
Assistant Examiner—J. L. Kruter
Attorney, Agent, or Firm—Arthur Dresner

[57] ABSTRACT

This invention teaches a hand-held surgical instrument for performing ophthalmological incisions in the form of an arc of a circle, which are particularly suited for cataract surgery in order to provide access to the anterior chamber of a human eye to allow removal of a cataract lens. The instrument includes a fixation assembly having a pair of elongated arms fixed to each other at one end thereof, the other ends thereof being movable toward and away from each other. A pair of prongs are carried at the movable ends of the arms for insertion into the globe of the eye so that the surgeon may hold the eye in a fixed position. A linkage assembly is connected at one end to the fixation assembly and a knife assembly is connected to the other end of the linkage assembly for pivotal movement about a pivot point. The knife assembly includes a knife blade holder and a knife blade with a cutting edge at one end thereof carried in the holder. With one hand, the surgeon will hold the fixation assembly immobilizing the eye and supporting the instrument in proper position. With the other hand, the surgeon will cause the knife blade and holder to pivot through an arc of a circle and will apply sufficient pressure thereto so that the cutting edge will penetrate the eye and describe an incision in the form of an arc of a circle.

19 Claims, 16 Drawing Figures

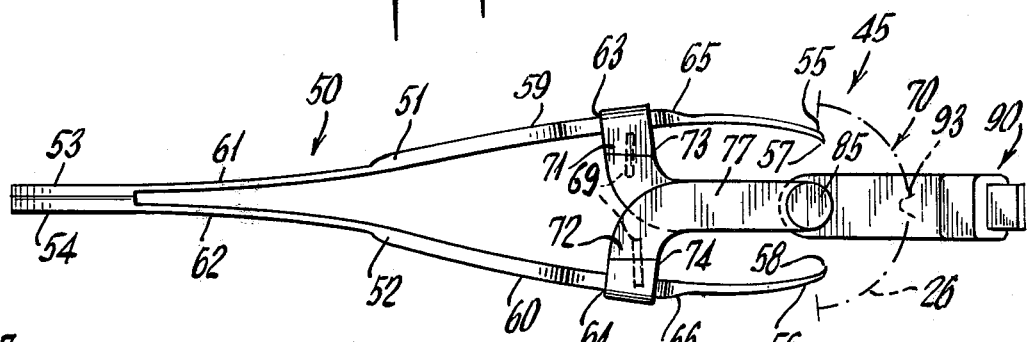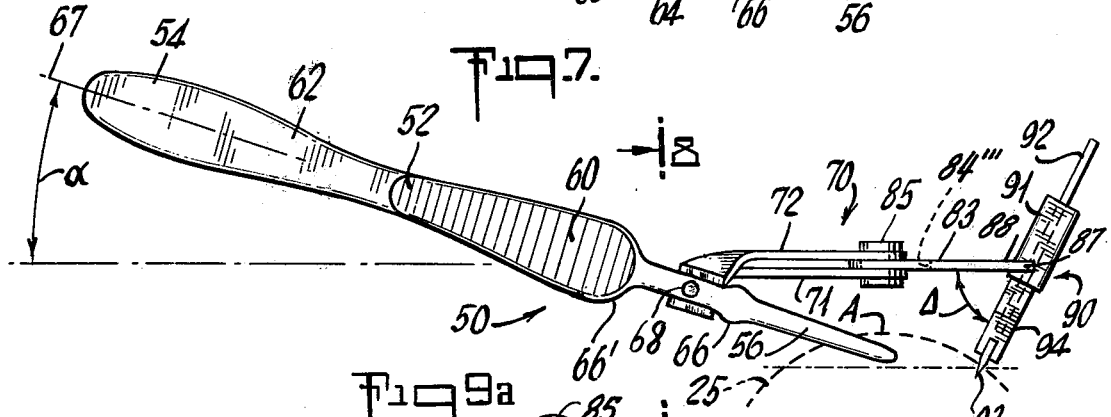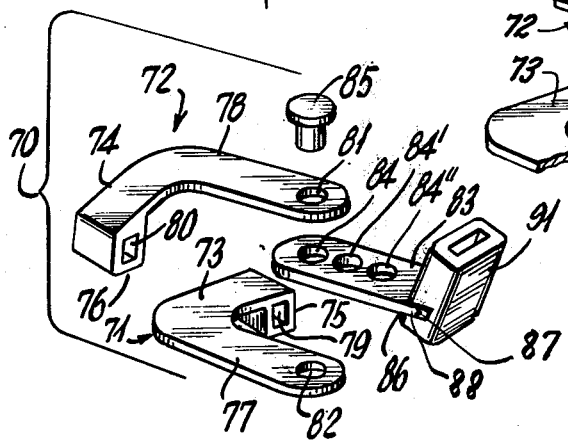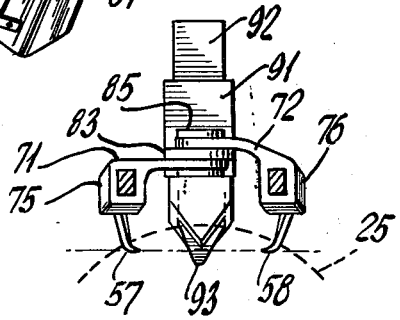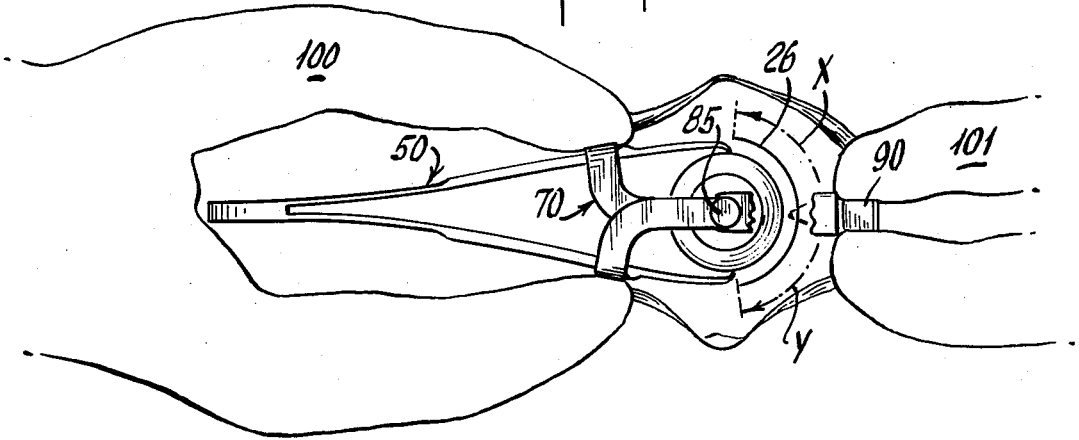

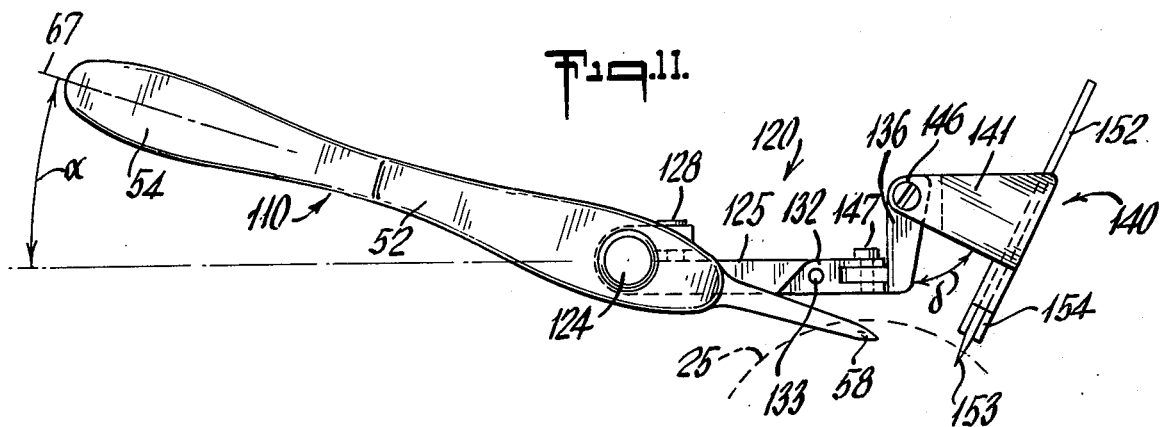
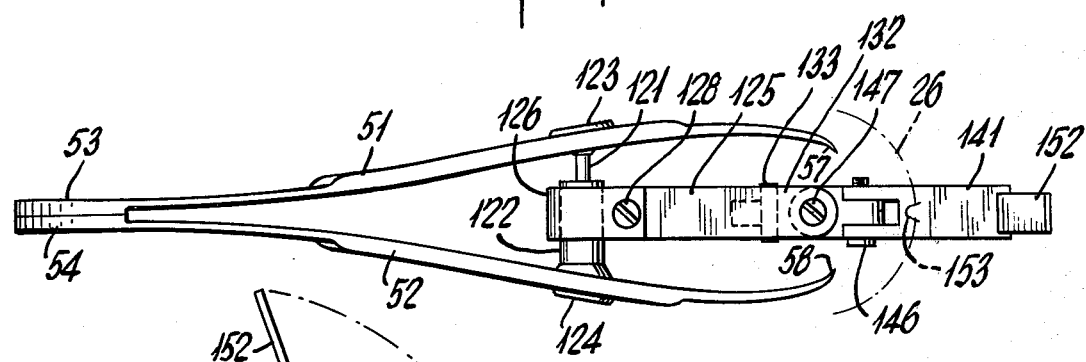
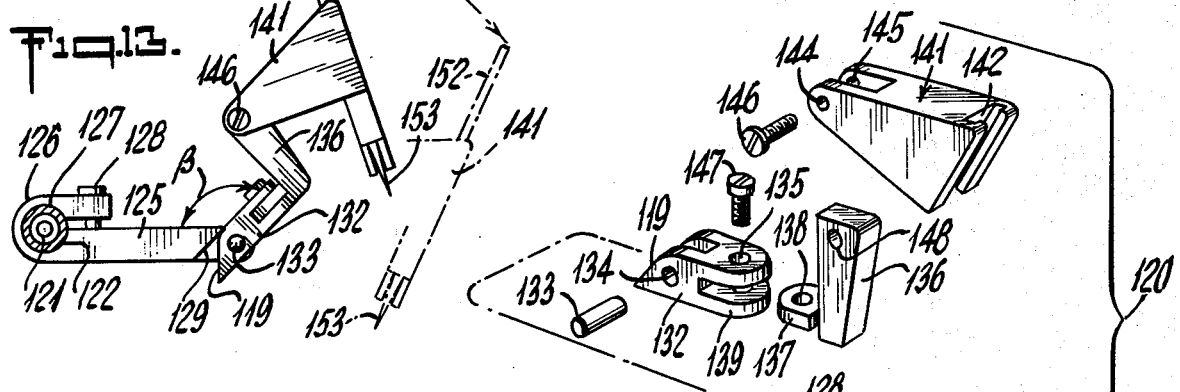
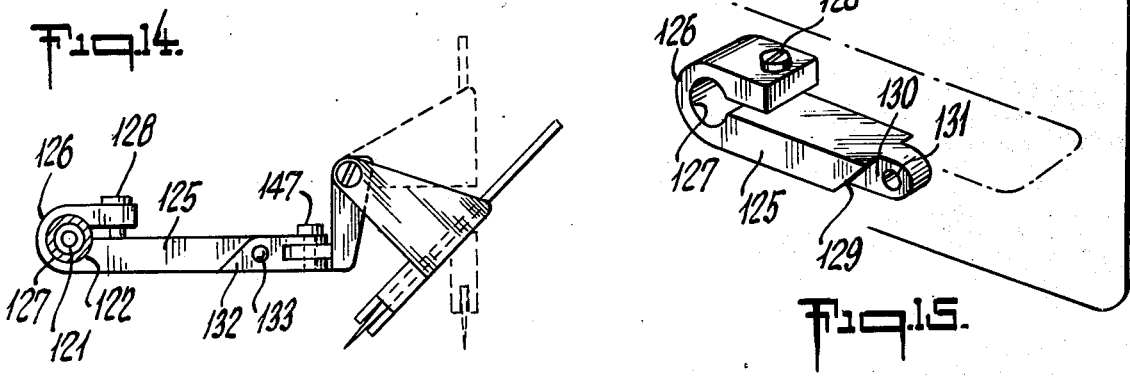

OPHTHALMOLOGICAL SURGICAL INSTRUMENT

BACKGROUND OF THE INVENTION

This invention relates generally to the field of surgical instruments and more particularly is directed to a hand-held surgical instrument used for describing an occular incision particularly suited for cataract surgery in order to obtain access to the cataract lens.

A cataract lens, or one which has become partially or wholly opaque, sometimes requires removal from the eye depending upon a variety of circumstances which are taken into consideration by the ophthalmic surgeon. Once a decision has been made to remove the cataract lens a variety of techniques have been developed and are available depending upon the particular condition of the lens material itself. Two such known techniques are: "extracapsular cataract extraction" and "intracapsular cataract extraction".

Ultrasonic cataract remova is one form of extracapsular extraction. This involves the insertion of an ultrasonic probe into the lens material and activating the probe for emulsifying the lens. The emulsified material can then be aspirated by a variety of electronic and hydraulic equipment. Examples of such techniques can be seen in U.S. Pat. Nos. 3,589,363 and 3,857,387.

A variety of vibrating tools, suction devices, hydraulic implements, and electronic controls have been developed and are required for cataract removal when using the ultrasonic removal techniques.

Because, however, of the delicacy of the positioning of the probe, the use of complex and costly electronic or hydraulic equipment, possibilities of complications in post operative care, the degree of skill required to ensure complete fragmentation of the lens material and subsequent aspiration of the emulsified material, and a variety of other reasons, the ultrasonic cataract removal techniques have not become as widely used as originally anticipated.

Additionally, the use of the ultrasonic technique must be limited to removal of cataract lenses which are either congenital, up to approximately the age of 20 or to those in which the consistency of the lens is still semifluidic. However, when the lens material becomes hardened ultrasonic emulsification and subsequent aspiration is difficult if not impossible. In such situations, the more traditional technique of intracapsular extraction is preferred. Furthermore, it is believed that intracapsular cataract extractions involve less possibility of post operative complications and provide greater opportunity for ensuring complete removal of the cataract lens element.

Therefore, removal of cataract lenses by the intracapsular technique is still a popular if not the preferred method amongst ophthalmic surgeons. In the intracapsular extraction technique, a conjunctive flap is first formed by making an incision in the conjunctiva so that it may be moved back to expose the sclera of the eye at the corneal border.

In order to obtain access to the cataract lens, which is located behind the cornea, an incision is then formed extending approximately between 140° and 180° around the cornear in the limbus area and desirably spaced 0 to 2 mm from the periphery of the cornea. The various types of locations of this incision is described at some length in *Cataract Surgery And Its Complications* by Norman S. Jaffe, the C. V. Mosby Company St. Louis 1972. One of the more desirable types of incisions is a multiplane incision in which a first cut (in a first plane) extends only partially through the thickness of the eye. This partial thickness incision is commonly referred to as a "cataract groove". Second, and sometimes third incisions, in second and third planes, are then made to enter the anterior chamber for access to the lens. The first incision or groove typically extends to a depth of approximately one-half the thickness of the wall of the eye globe by use of a rounded scalpel blade, razor blade or other instrument, either perpendicular to the wall of the globe or at an angle beveled to the surface of the globe. The initial incision or groove may be enlarged with either a scissor, keratome or other blade implement. Once the entire incision is completed, the cornea may be lifted or retracted to gain access to the anterior chamber. The cataract lens may then be extracted through the use of any number of techniques, such as cryo extraction (the formation of an ice ball in contact with the lens capsule formed at the tip of a cryo probe) or by gripping the lens by a forceps device. The techniques for lens extraction are described more fully in the above mentioned *Cataract Surgery And Its Complications.*

The groove, or multiplane type of incision, has a number of advantages over an incision which lies in a single plane and extends through the full thickness of the eye into the anterior chamber. First, after the groove is formed, radially arranged sutures may be preplaced across the groove before the entire incision is completed so as to insure exact lateral realignment after the operation. Preplaced sutures also allows the surgeon the option of quickly closing the wound at any time during the procedure should circumstances demand that the wound be so closed. Secondly, a multiplane incision provides control over depth realignment, whereas a single plane incision involves possible difficulties in exact depth repositioning of the opposing sides of the incision with respect to each other.

Because the groove (first incision) has heretofore been typically formed by free hand, no two grooves can ever be expected to be exactly the same. Accordingly, results and post operative effects cannot be accurately anticipated. In addition, because the free hand groove can never be perfectly semi-circular, the placement of sutures in often a difficult procedure.

In addition to the lack of uniformity created by free hand describing of the groove, the surgeon often has difficulty in completing the full 140°-180° incision since the cutting edge is usually supported in a holder which is gripped by the surgeon in one hand, while he stabilizes the globe of the eye through the use of a fixator or forceps element carried in the other hand. Accordingly, it is necessary for the surgeon to both rotate the globe using the fixator in one hand while rotating the position of the cutting edge with the other hand, often finding himself in an awkward position and unable to complete the groove in a single sweeping motion. This frequently results in a groove which is either not smooth or which may not be positioned in the desired location.

It should be noted, that while the groove or multiplane incision is desired, the present invention may be used with satisfactory results to accomplish either a groove or a full thickness incision.

One recent attempt to overcome some of the foregoing disadvantages of forming a groove free hand is described in an article in the 1975 Fall Issue (Volume 6, No. 3) of the periodical Ophthalmic Surgery, by James T. Pattern entitled "Groove Maker for Cataract Surgery". The instrument described in this article was formed by modifying a corneal trephine. The diameter of the cutting edge was split to form a curved cutting surface having an arc of approximately 100° and a radius of curvature of 6 mm. The curved cutting surface is then applied to the desired position on the limbus and then twisted back and forth by free hand movement of the surgeon to complete the desired 140°-180° groove. While the use of this instrument would appear to be an advance in the formation of the cataract groove it still requires a certain degree of free hand movement and judgment in the placement of the cutting surface.

It is accordingly a general object of the present invention to provide an instrument for forming a cataract groove which overcomes all of the disadvantages of the prior art.

It is a further and more specific object of the present invention to provide and ophthalmic surgical instrument used in surgery for removing cataract lenses from the eye be enabling the surgeon to describe an incision concentric with the cornea of predetermined radius and uniform curvature, depth and angle with absolute accuracy and consistency for each operation performed.

It is yet another object of the present invention to provide an improved means for forming an incision in the wall of the eye to permit access to the anterior chamber for removal of cataract lenses.

A still further object of the present invention is to provide an instrument having means for fixing the globe of the eye and means to describe an incision with respect to the periphery of the cornea determined by the position of the fixating element.

The above objects, features and advantages, along with other objects, features and advantages of the present invention will become more apparent from the detailed description of the invention in conjunction with the accompanying drawings to be described more fully hereinafter.

SUMMARY OF THE INVENTION

The present invention is directed to a hand-held surgical instrument to facilitate the making of the "cataract groove" or incision required during the intracapsular technique of cataract lens removal.

The instrument of the present invention for performing ophthalomological incision in the form of an arc of a circle includes a fixation assembly having a pair of elongated arms fixed at one end thereof to each other so that the other ends thereof are movable toward and away from each other, a prong carried at the other end of each of said elongated arms for insertion into the globe of a human eye, and finger grip means on the pair of arms so that the instrument may be held in one hand of a surgeon to grip the eye therewith. A linkage assembly is connected to at least one of the arms of said fixation device. A knife assembly is connected to the linkage assembly, and comprises a knife blade holder, a knife blade removably carried by the knife blade holder, and a cutting edge carried at one end of the knife blade for making an incision in the eye of a patient. The knife assembly is connected to the linkage assembly for pivotal movement about a pivot point on the linkage assembly so that the knife blade holder may be moved through an arc of a circle by the other hand of the surgeon, and so that the cutting edge will penetrate the eye and describe an incision in the form of an arc of a circle when sufficient pressure is applied thereto. The knife assembly is also preferably connected to the linkage assembly for pivotal movement about an axis so that the angle of inclination of the cutting blade to the globe of the eye may be varied.

In one embodiment the linkage assembly comprises first and second "L" shaped linkage arms, each the arm having first and second legs, the distal end of the first leg of each arm being connected to one of the elongated arms of the fixation assembly, the distal end of the second leg of each of "L" shaped arms being pivotally connected together defining said pivot point, and a third linkage arm pivotally connected at one end thereof to the second leg of the first and second linkage arms at the pivot point, the knife assembly being carried at the other end of the third linkage arm so that the knife blade and cutting edge may be pivoted about the pivot point by pivotal movement of the third linkage arm thereabout.

In a further embodiment of the invention the linkage assembly comprises a piston connected to one of the elongated arms of the fixation assembly and extending toward the other of the elongated arms. A cylinder is connected to the other arm of the fixation device for carrying the piston so as to damp the movement of the elongated arms of the fixation assembly toward and away from each other. A first linkage arm is supported at one end thereof on said cylinder for adjustable pivotal movement thereabout. Means are carried by the first linkage arm for preventing pivotal movement thereof about the cylinder so as to adjust the position of the first linkage arm on the cylinder. A coupling member is pivotally carried at the other end of the first linkage arm for pivotal movement in a first plane so as to vary the angle of the coupling member with respect to the longitudinal axis of the first linkage arm. A second linkage arm is connected at one end thereof to the coupling member at a pivot point for pivotal movement thereabout in a second plane. The knife assembly is carried at the other end of is second linkage arm so that the knife blade and cutting edge may be pivoted about the pivot point by pivotal movement of the second linkage arm thereabout.

The foregoing and other features of the cataract groove cutting surgical instrument and the various other elements of the present invention are more fully described with reference to the following drawings annexed hereto.

BRIEF DESCRIPTION OF THE DRAWINGS

FIG. 6 is a plan view showing a first embodiment of the invention when positioned for use on the globe of a patient's eye to perform the cataract incision;

FIG. 7 is a side elevational view of the embodiment of the invention shown in FIG. 6 in the same position for operative use;

FIG. 8 is a sectional view taken along lines 8—8 of FIG. 7 showing the position of the various elements of the embodiment shown in FIGS. 6 and 7 with respect to the patient's eye;

FIGS. 9 and 9a are partial exploded views showing the positional relationship of various elements of the embodiment of the invention shown in FIGS. 6 through 8;

FIG. 10 is a plan view showing the manner of use of the invention shown in the embodiment of FIGS. 6 through 9;

FIG. 11 is a side elevational view showing a further embodiment of the present invention positioned for use with respect to the human eye to perform the desired cataract incision;

FIG. 12 is a plan view of the embodiment shown in FIG. 11 indicating the manner of use to perform the incision on the human eye;

FIGS. 13 and 14 are partial elevational views showing a portion of the surgical tool of the present invention as shown in FIG. 11 indicating various positions thereof to facilitate use; and FIG. 15 is an exploded view of a portion of the invention shown in the embodiment of FIGS. 11 through 14.

DESCRIPTION OF THE INVENTION

Figure 1:
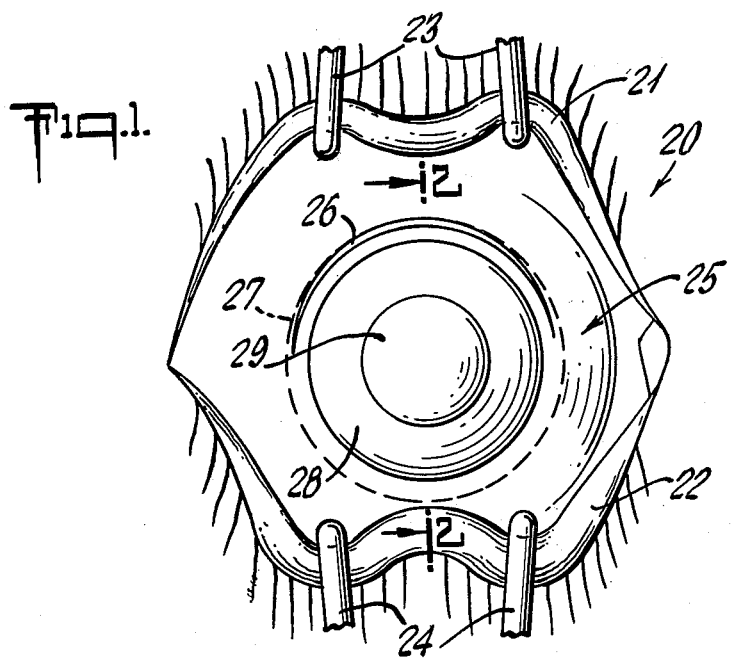
FIG. 1 is a plan view of the globe of the eye with eyelids shown in a retracted position and showing desired location of the cataract groove to be performed with the present invention.
Figure 2:
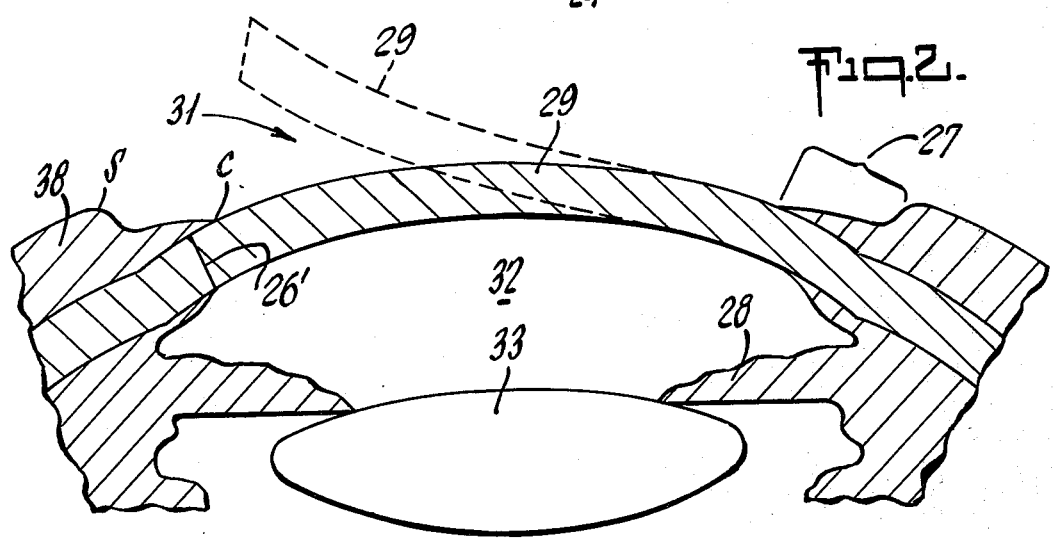
FIG. 2 is an enlarged sectional view taken along lines 2—2 of FIG. 1 showing in somewhat schematic representation the position of the lens to be removed by the cataract surgery, the position of the cataract incision or groove, and the formation of the flap to provide access to the anterior chamber for removal of the lens.
Figure 3:
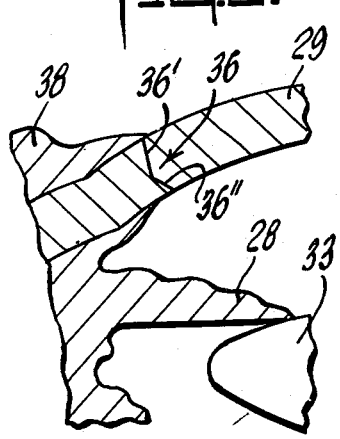
FIGS. 3, 4 and 5 are partial sectional views similar to the view of FIG. 2 and showing various types of cataract incisions which may be performed using the present invention.

Referring now in greater detail to the accompanying drawings, FIG. 1 shows in plan view a representation of a human eye as prepared for surgery to remove a cataract lens. The eye, indicated generally by reference numeral 20 includes upper and lower eyelids 21 and 22 respectively which are held in a retracted position by a pair of commonly used lid retractors 23, 24 which are commercially available such as from the Storz Instrument Company under Catalog Nos. E-996, E-997, E-998 1 or E-1000. Retraction of the eyelids reveals a major portion of the globe 25 of the human eye so as to provide sufficient room for the surgeon to prepare the eye for removal of the cataract lens by performing the incision indicated as reference numeral 26, which may be a full thickness incision 26' (FIG. 2) or a groove 36' (FIG. 3).

The particular radius of curvature of the incision and the radial placement of the groove or incision with respect to the border of the cornea will depend upon a number of objectives of the surgeon. However, in cataract surgical procedures utilizing the groove technique, it has, as hereinbefore indicated, been common practice to perform the groove by free hand incision utilizing a scalpel and describing an arc in the desired position by swinging the surgeon's hand through approximately 180°. Such a circumferential arc is difficult to complete in a single sweep of the surgeon's hand and accordingly it has been found that grooves performed in this manner frequently do not fall along an exact circumferential line of a circle, are frequently irregular, and rarely are two grooves ever identical even though performed by the same surgeon. As hereinbefore noted, it is therefore the principle object of the present invention to enable the surgeon to perform a cataract incision by a single sweep of his hand and to be assured that the incision will be an exact arc of a circle, be exactly regulr with no broken lines, and will be exactly the same for each operation regardless of which surgeon performs the incision. In this manner, the operation can easily become standardized, will insure expected post operative results and will tend to minimize complications in performing the surgery.

For purposes of explanation and understanding the present invention, the incision 26 shown in FIG. 1 has been placed in the area of the limbus 27, the posterior border of which is indicated generally by a broken line in FIG. 1. While the limbus portion of the human eye may differ with individuals, it generally extends a radial distance of approximately 2 mm from the circumferential border of the iris 28. It has been found that placing the cataract groove in the area of the limbus produces desirable results although other types of incisions have also met with success.

In viewing the human eye shown in FIG. 1, retractor 23 is positioned on the upper eyelid (the one toward the patient's forehead), while retractor 24 is positioned at the patient's lower eyelid (the one adjacent the patient's cheek). Accordingly, the groove 26 will extend for approximately 180° from about the 9 o'clock position, through the 12 o'clock position, and terminating at approximately the 3 o'clock position. This type of groove, if performed free hand would require an unusually steady hand and a change in the position of the surgeon's hand when passing through about the 12 o'clock position since a change in direction occurs at about this point. The use of the present invention, however, makes the formation of this groove a relatively simple matter regardless of the skill of the surgeon in describing the type of arc required for the cataract groove.

Prior to actually forming the groove, an incision is preferably made in the conjunctiva 38 in the area of the limbus and desirably at the corneal border. This will allow the surgeon to form a conjunctive flap so that it may be removed to provide access to the limbal area in order to form the groove.

After the incision 26 is completed the cornea 29 may be lifted away from the globe of the eye (shown in dashed lines in FIG. 2) so as to provide an area of access 31 to the anterior chamber 32 for removal of the cataract lens 33 through the area of access 31.

A variety of locations may be chosen for the groove in the limbus area. The location of the incision 26' shown in FIG. 2 is at approximately the mid-limbal area. A groove or incision placed anteriorly of the position indicated by the letter C will lie on the cornea, i.e. a corneal groove, while a groove placed past the posterial limbal border, such as at position S, is one known as a scleral groove since it will be positioned at a point in the sclera of the eye rather than in the limbus area.

Where to position the groove or whether to use a full thickness incision, are decisions to be made by the surgeon. No matter where the location of the groove, the present invention will provide the surgeon with the ability to perform an incision having a uniform radius of curvature and will be identical with each operation.

In addition to choosing the particular location of the incision, a variety of types of incisions may also be used. These are described in detail in the above mentioned text by Norman S. Jaffe in Chapter 4 entitled "Surgical Technique". Four different types of incisions are shown in FIGS. 2 through 5 respectively and each of these types of incisions can be performed, at least in part, by using the present invention.

In FIG. 2, a full thickness incision 26' is shown as a "perpendicular" incision. In other words, this incision extends throughout its length at a position perpendicular to a plane tangent to the globe of the eye at the point of incision. Depending on the particular limbal location of this incision 26', access can be had directly into the anterior chamber.

FIG. 3 shows a further type of incision indicated by reference numeral 36, and referred to as "perpendicular-beveled". In this type of incision a first perpendicular portion 36' (the groove) is made using the present invention and extends to a depth of approximately one-half the thickness of the wall of the globe or slightly greater. The depth of the incision to be made, using the present invention, can be determined by a guard element on the knife edge, to be described more fully hereinafter. The anterior chamber is entered by forming a beveled portion 36" by enlarging the perpendicular portion of the incision with a scissors held at an angle of approximately 45° to the wall of the globe. Once, however, the perpendicular portion 36' (the groove) has been formed by using the present invention, uniformity of the radius of curvature of the incision has been established so that the use of a further instrument such as scissors will not have a detrimental effect on the curvature of the incision. Also, as previously noted, sutures may be preplaced across the groove before completing the beveled portion 36".

Figure 4:
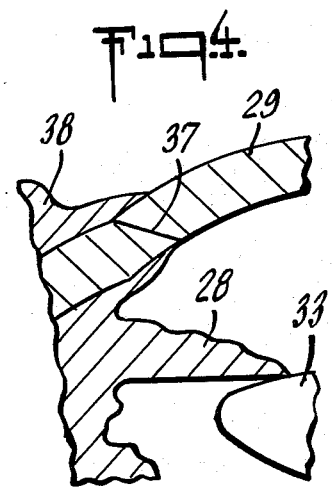

FIG. 4 shows a "beveled" incision indicated by reference numeral 37, which has many advantages over other types of grooves with respect to ease of suturing and ease of performing. The present invention is uniquely suited to performing this type of incision as will be appreciated more fully in the description to follow.

Figure 5:
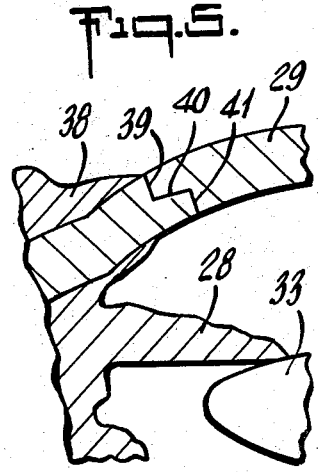

FIG. 5 shows a further type of incision referred to as a "four-plane incision", the first being an incision in the conjunctiva to form the conjunctive flap so that the conjunctiva 38 may be moved away to provide access to the limbal area so that the groove can be formed. The second incision 39 is a perpendicular incision (the groove) to be performed using the present invention so as to establish a uniform curvature for the groove. The third plane 40 extends perpendicular to the plane of the incision 39 and toward the cornea for a distance of approximately 1 to 2 mm, and the fourth plane 41 is a deep perpendicular incision into the anterior chamber.

FIGS. 6 through 10 basically show a single embodiment of the present invention with some variations, which is referred to generally as reference numeral 45 and generally comprises three basic elements or substructures. The first element 50 is a fixation device and is used as a means by which the surgeon will engage the globe of the human eye in order to fix its position while the groove or incision is being formed. This is a significant element of the present invention in that it enables the surgeon to both prevent movement of the globe of the eye while performing the incision and also provides a means for establishing a fixed point of reference for positioning the cutting blade to be defined more fully hereinafter.

One type of fixation device found to be satisfactory for the purposes of the present invention is a device similar to commonly used forceps, a tong-like device for delicately but firmly holding a particular item. The fixation device envisioned for use in the present invention comprises a pair of arms 51 and 52, each of which are preferably made of spring steel and each of the arms 51 and 52 are fixed to each other at 53 and 54 respectively while the opposite or distal ends 55 and 56 respectively are free to move toward and away from each other. The upper shank portions 61 and 62 of each of the arms may be pre-stressed so that movement of the arms toward or away from each other will result in return of the arms to an original position. Each of the arms is also provided with a finger grip area 59 and 60 having a roughened or non-slip surface so that the surgeon will be able to hold the fixation device between his fingers without its slipping therefrom. The free or movable ends 55, 56 carry prongs 57, 58 each of which are approximately 2 mm long so that when the fixation device is used by the surgeon the prongs will be forced to partially penetrate the sclera of the globe of the eye. so that the surgeon will have a firm grip thereon in order to fix the position of the globe and prevent rotation or movement thereof during the incision procedure.

The knife assembly 90 forms the second basic element of the invention and includes a knife blade holder 91 and the knife itself 92 carried therein. The knife may be of the commercially available type, such as the commonly used Beaver Knives sold by the Storz Instrument Company. One such suitable knife is the Storz Beaver Knife sold under Catalog No. E-359-54A and such as disclosed in U.S. Pat. No. 3,945,117. The knife has a cutting edge 93 and an adjustable plastic guard 94 used to vary the exposure of the blade 93 so as to adjust the depth to which the cutting edge will enter the limbus area of the eye. In this manner the various types of incisions shown in FIGS. 2 through 5 can be easily achieved. For example, in order to accomplish the incision known as the "perpendicular" incision the cutting edge will have to be exposed to a depth sufficient to allow the blade to cut entirely through the sclera and enter the anterior chamber. In performing a "perpendicular-beveled" incision, however, the plastic guard 94 will be adjusted so that the depth of cut will only be sufficient to perform the perpendicular portion of this type of incision. This type of knife, which carries the plastic guard to adjust the depth of cut, has been found to be most suitable for this type of surgical instrument.

The third basic element of the present invention is the linkage assembly, referred to generally as reference numeral 70. This element serves to link the knife assembly 90 with the fixation device 50 in order to provide a fixed relationship therebetween to establish a constant radius of curvature upon which the knife blade will be described. In order to accomplish this, the linkage assembly comprises first and second "L" shaped arms 71 and 72 each having short legs 73, 74 and long legs 77, 78 respectively. Each of the short legs 73, 74 carries means such as sleeves 75, 76 respectively for joining the "L" shaped arms to the fixation device 50 at lower shank portions 63, 64 respectively.

In the embodiment shown in FIGS. 6, 8 and 9, each of the sleeves 75, 76 is provided with square or rectangularly shaped openings 79, 80 for connection to the fixation device. The lower shank portions 63, 64 of the fixation device are accordingly complementarily square or rectangularly shaped so that when the "L" shaped arms are carried on the fixation device they will not be able to rotate or otherwise move out of a predetermined position. Additionally, the lower shank portion of each of the arms 51, 52 of the fixation device 50 carries upper and lower abutment elements 65, 65' and 66, 66' to prevent axial movement of the "L" shaped arms along the fixation device. Apertures 81 and 82 are located at the distal end of long legs 77, 78 respectively. Apertures 81 and 82 are aligned with each other when the "L"

shaped arms 71 and 72 respectively are connected to the fixation device.

In order to provide flexibility in placing the instrument in a fixed position of the globe and allow for fine adjustment in locating the cutting edge in a desired position on the limbus, pivotal connection between short legs 73, 74 and the arms of the fixation device may be provided. This can be accomplished by legs 73 and 74 being segmented into two parts with the segments pivotally connected by pivot pin 69 (as seen in FIG. 6). Alternatively, sleeves 75, 76 can be eliminated and short legs 73, 74 directly pivotally connected to the arms of the fixation device by rivets 68, which is shown as an alternative embodiment in FIG. 7. The linkage assembly can thus be pivoted about either the axis of pins 69 or about rivets 68. In this manner, after the surgeon places the fixation device in a desired position and causes prongs 57, 58 to penetrate the globe, fine adjustment for proper placement of the cutting edge in the limbus area can be accomplished by such pivotal movement.

A further linkage arm 83 has an aperture 84 at one end thereof so that it may be connected to the "L" shaped arm 71, 72 by a rivet or pin 85 passing through apertures 81, 82 and 84 so as to join all three links together at a pivot point defined by the rivet 85. The other end 86 of the linkage arm 83 is connected to the knife assembly and preferably carries the knife holder 91.

When the "L" shaped arms 71, 72 are connected to the fixation device as described above, and the linkage arm 83 is connected at its end to the distal ends of the "L" shaped arms, a linkage assembly is formed between the fixation device and the knife such that the knife may be moved by one hand by the surgeon in an arc, the constant radius of which is determined by the length of linkage arm 83 so that a smooth and uniform cataract groove or incision, as indicated by dot-dash lines 26 in FIG. 6 may be formed.

The use of the invention as shown in the embodiment of FIGS. 6 through 10 may best be appreciated from FIGS. 7, 8 and 10. Using one hand, indicated by reference numeral 100, the surgeon will first grip the fixation device between the fingers of that hand moving the arms 51 and 52 apart where necessary so that the prongs 57, 58 may be placed on the desired position of the globe of the eye. The surgeon will then apply sufficient pressure to the arms 51, 52 so that they will be moved towards each other and so that the prongs 57, 58 will pierce the sclera and penetrate to a depth sufficient for the surgeon to maintain the fixation device in place with little additional pressure, thus fixing the globe of the eye of the patient and also determining the approximate radius of curvature of the groove to be described. The exact radius is determined by exact positioning of the cutting edge after fine adjustment by pivotal movement of the linkage assembly about pivot pins 69 or rivets 68. In moving the arms toward and away from each other, the "L" shaped arms 71, 72 will move in a scissor like manner about the pivot point defined by the rivet 85. Once the fixation device, however, is in place, no further movement of the arms 71, 72 will take place.

It will be seen from FIG. 7 that in placing the fixation device in the desired position, the longitudinal axis 67 will be positioned at an angle (less than $\alpha$) with respect to a horizontal plane which will be parallel to a plane tangent to the globe of the eye at the center of the cornea (a point indicated by the reference letter A). After the fixation device is in position, in order to bring the cutting edge of the blade 92 into contact with the globe 25, the surgeon will rotate or pivot the fixation device about the point where the prongs have penetrated the globe until the axis 67 reaches the angle $\alpha$ with the horizontal plane, defined above, at which point the knife blade 93 will penetrate the sclera to the desired depth as determined by the axial position of the guard. The surgeon may also bring the blade into contact with the globe by pivoting the linkage assembly about the pivot pins 69 or rivets 68. With the fingers of the other hand, indicated by reference numeral 101, the surgeon will then grip the blade 92 and move it first in one direction, indicated by arrow X, and then in the opposite direction, indicated by arrow Y (see FIG. 10), until the groove 26 has been formed. The surgeon will move the blade in the desired directions over an arc of approximately 180°. The radius of that arc will of course be exactly determined by the length of the linkage arm 83 so that the groove 26 will be exactly uniform.

In order to ensure that the groove is in the desired limbal area, the dimensions of the various links will be designed such that when the pivot point, defined by the rivet 85, is placed in substantial alignment with the center of the cornea A, the knife blade 93 will penetrate at the desired location. Since the dimensions of all human eyes, and the various elements thereof are substantially identical, the cornea being substantially circular with a radius of about 6 mm, and since the limbal area is approximately 2 mm wide, the knife blade will enter the globe at a distance of approximately 7 mm-8 mm from the center of the cornea A, in order to perform a mid-limbal incision. Fine adjustment of this placement is made possible by the pivotal mounting of the linkage arms 71, 72 with respect to the fixation device.

It will also be noted from FIG. 7 that the short legs 73, 74 of the L shaped arms are twisted through an angle so that the long leg portions thereof 77, 78 will lie in a plane parallel to each other and parallel to the plane of the linkage arm 83. The degree of twisting these short legs, however, can be varied, in which event the angle $\alpha$ will vary. Angle $\alpha$ is also easily varied when the instrument is provided with means (such as segmented short legs 73, 74 and pivot pin 69, or rivet connection 68) to pivotally connect the linkage assembly to the fixation device.

An additional refinement of the embodiment shown in FIGS. 6 through 10 would be to add a further degree of flexibility by providing means to vary the angle of the knife blade holder 91 with respect to the plane of the linkage arm 83 so that more than just one type of incision can be performed with the same instrument. This can be accomplished in a number of ways, such as is shown in FIG. 9, by forming linkage arm 83 with a bifurcated end 88 having pivot pins or rivets 87 engaging the knife blade holder so that the angle can be changed. Together with pivotal connection of the linkage arms to the fixation assembly, as hereinbefore described, fine adjustment for proper placement of the incision in the limbus is possible.

Additionally, it may in certain instances be desirable to vary the distance of the knife blade from the pivot point or rivet 85. This may further be accomplished by mounting the knife blade holder 91 in a sliding arrangement on the link 83 such as shown in FIG. 9a. Here a slot 84''' is provided in link 83 to allow varying the distance of knife holder 91 from the pivot point. Some other means for varying this distance, such as providing a plurality of apertures 84', 84", etc., through which pin 85 may pass to mount arm 83 can also be provided (see FIG. 9a).

The embodiment shown in FIGS. 11 through 15 also includes means to provide the greatest degree of flexibility, ease in use, and adaptability for various types of incisions which any particular surgeon may desire to make.

The embodiment shown in FIGS. 11 through 15 comprises the same three basic elements as included in the embodiment of FIGS. 6 through 10 to wit: a fixation device 110, a knife blade assembly 140 and a linkage assembly 120 connecting the knife blade assembly 140 with the fixation device 110.

The fixation device 110 of this embodiment is substantially identical to the fixation device shown in the embodiment of FIGS. 6 through 10 and accordingly like reference numerals will denote like parts. Hence, the fixation device 110 includes arms 51 and 52 which are joined at one end 53,54 and have prongs 57,58 at the other end.

The knife blade assembly 140 includes a holder 141 and a knife 152 therein. The knife 152 may be the same type of knife described with respect to the embodiment shown in FIGS. 6 through 10 (i.e. the Beaver Knife shown in Storz Catalog No. E-359-54A) with a plastic guard 154 and cutting edge 153.

The knife blade holder 141 shown in the exploded perspective view of FIG. 15 has a slot 142 to accommodate therein the knife 152. The knife holder also has a bifurcated end 143 with aligned holes 144, 145 for pivotal attachment to the linkage assembly as will be described hereinafter. In this manner, the knife blade holder can be pivoted toward and away from the patient's eye so as to provide an additional means of adjustment and ease in bringing the knife blade into contact with the surface of the sclera.

Because of the variety of types of incisions available to surgeons and because of likely differences in placement of the fixation device, minor differences in dimensions of a particular patient's eye and other variations, it is desirable that the linkage assembly have the various types of adjustments to be described hereinafter with respect to this embodiment so that the surgeon will have the facility to account for such minor variations.

Accordingly, the linkage assembly of the present embodiment includes a piston and cylinder arrangement for connection to the fixation device 110. Cylinder 122 is accordingly connected to arm 52 such as by a rivet 124 and piston 121 is connected to arm 51 such as by rivet 123. Piston 121 may either be spring loaded within the cylinder or pneumatically loaded therein so as to dampen the movement of arms 51 and 52 so that they may be held apart and only a small amount of hand pressure exerted by the surgeon is required to bring those arms together for causing prongs 57 and 58 to penetrate the sclera for fixation.

A first linkage arm 125 is carried on the cylinder 122 for pivotal movement thereabout. The arm 125 has a substantially "U" shaped end 126 with opening 127 through which the cylinder may be positioned. A set screw 128 is provided in one leg of the "U" shaped end so that the arm 125 may be secured on the cylinder 122 without allowing for free pivotal movement. The screw 128 may be loosened for adjusting the position of the arm 125 on the cylinder to vary the angle at which the fixation device may be held by the surgeon.

The other end of the arm 125 is provided with shoulders 129 and an extended flange 130 carrying an aperture 131 (see FIG. 15). A universal coupling member 132 is pivotally connected to the arm 125 by a pivot pin 133 passing through apertures 134 on the coupling 132 and the aperture 131 on the flange 130 of the arm 125. In this manner, the coupling member 132 may be pivoted about the pin 133 to vary the angle thereof with respect to the arm 125 such as shown in FIG. 13. Abutment surfaces 119 cooperate with shoulders 129 to determine the maximum angle $\beta$ between arm 125 and coupling 132.

The other end of the universal coupling 132 is also bifurcated having apertures 135.

A second linkage arm 136 has a flange 137 with aperture 138. The flange 137 will fit between the bifurcated ends 139 of the coupling element 132 and be held therein for pivotal movement by pin 147. The pin 147 is preferably a threaded screw with apertures 135 having internal threads to receive the screw 147. At the end of the second linkage arm 136 opposite to the flange 137 is a second aperture 148. The end of the linkage arm 136 carrying aperture 148 is arranged to fit between the bifurcated ends 143 of the knife holder 141. In this manner, the knife holder 141 is mounted for pivotal movement on the linkage arm 136 by pivot pin or screw 146.

In using the invention shown in the embodiment of FIGS. 11 through 15, the surgeon will first position the fixation device 110 by piercing the sclera with prongs 57,58 so that the axis of the pivot pin 147 is as nearly aligned with the center of the cornea as possible. This will place the knife holder in approximately the desired position of the limbus area for the surgeon to make the incision and complete the groove. In order to set the fixation device at the desired angle of comfort for use by the surgeon, the coupling element 132 may be pivoted about pin 133 until the desired angular relationship (represented by the angle $\beta$-see FIG. 13) is achieved. When the angle $\beta$ is at its maximum 180° (as determined by abutment surfaces 119 engaging shoulders 129), such as shown in FIG. 11, the axis 67 of the fixation device will have to be at the angle $\alpha$ when the knife holder 140 is held in the position of angle $\gamma$ with respect to the second linkage arm 136 for the knife cutting edge 153 to make the incision. Varying the angle $\beta$ will allow the surgeon to vary the angle $\alpha$ to a position which is most comfortable for his use. By providing the universal coupling 132 the angle $\alpha$ may be varied without affecting the positioning of the blade in the proper limbal area when the pivot pin 147 is properly aligned with the center of the cornea. Aligning the pivot pin 147, in the present embodiment (or the pivot pin 85 in the previous described embodiment), with the center of the cornea (point A—see FIG. 7) is fairly easily accomplished simply by setting the prongs 57, 58 at approximately the corneal boundary with the limbal area and positioning those prongs at approximately the 3 o'clock and 9 o'clock positions when the knife blade is at the 12 o'clock position.

After properly setting the fixation device at the desired angle for comfort, the knife blade may be brought into contact with the sclera for incision by pivoting the knife holder 141 about the pin 146, such as shown in FIG. 14. Additionally, varying the angular relationship of the holder 141 with respect to the linkage arm 136 will also allow the surgeon the flexibility of performing either a perpendicular type incision or a beveled type incision. After setting the fixation device and making the incision in the limbal area, the surgeon may then complete the groove by swinging or pivoting the second linkage arm 136 about the pivot pin 147 which will thus cause the knife blade holder 141 to similarly pivot about the pin 147 so that the blade will describe the desired arc forming the groove 26.

As with the embodiment shown in FIGS. 6 through 10, the present embodiment allows the surgeon to describe the cataract incision or groove with complete accuracy and uniformity because of the fixed relationship between the position of the blade and the center of the cornea as determined by the dimensions of the linkage assembly. Additionally, the present invention, as embodied in the structure shown in FIGS. 11 through 15 allows the surgeon the greatest degree of flexibility in positioning the knife cutting edge in the proper limbal area and maintaining the most comfortable position of the fixation device.

Further, by providing for the universal coupling 32 to pivot about pin 133, the blade holder and hence the blade 153 may be held out of position for cutting, such as shown in solid lines in FIG. 13 while the surgeon is setting the fixation device, and then for bringing the knife blade holder 141 and the blade forward to the position thereof shown in dot-dash lines in FIG. 13 so that the incision may be made.

FIG. 14 shows the manner in which the blade holder 141 may be pivoted about pin 146 so that the blade will be positioned either for a perpendicular or a beveled type of incision.

After completion of the incision, the cornea 29 may be lifted so that the anterior chamber may be entered and the lens 33 removed by means of a forceps or a cryo probe as discussed above.

The invention may be further modified by mounting the arm 136 and knife holder 140 of the embodiment shown in FIGS. 11-15, at the pivot point 85 in the embodiment of FIGS. 6-10. Additionally, the flange 137 may be extended and provided with a plurality of aligned apertures so that the distance between the pivot point and the knife may be varied by changing the aperture on flange 137 which pin 85 will pass through.

This type of modification provides all of the desired adjustments with the simplicity of the "L" shaped links, which have the advantage of insuring that pivot point 85 will be located over the center of the cornea if the prongs 57,58 are properly placed.

From the foregoing it will be appreciated that a novel surgeon's cutting instrument has been devised in which a cataract groove or incision can be made uniform and identical for each and every operation.

While the invention has been described and illustrated with respect to certain embodiments which produce satisfactory results, it will be understood by those skilled in the art, after understanding the purposes of the invention that various other changes and modifications may be made without departing from the spirit and scope of the invention, and it is therefore intended in the appended claims to cover all such changes and modifications.

What is claimed is:

1. A hand-held surgical instrument for performing ophthalmological incisions in the form of an arc of a circle centered on the cornea, said instrument comprising:

a fixation assembly having a pair of elongated arms which are fixed at one end thereof to each other, the other ends thereof being movable toward and away from each other, the pair of arms lying in common a plane which, when positioned for use, is at a minor angle to a plane tangent to the center of the cornea, a prong carried at said other end of each said elongated arms for insertion into the globe of the eye to fix the position of the arms, and finger grip means on said pair of arms so that the instrument may be held in one hand of the surgeon on one side of an eye to grip the eye therewith;

a linkage assembly connected to at least one of said arms of the fixation assembly and at a minor complementary angle to the fixation arm and, when positioned for use, extending therefrom above the eye in a plane approximately parallel to said plane tangent to the center of the cornea, the linkage assembly having a pivot point positioned equidistant from said prongs over the center of the cornea of the eye, the pivot point axis extending approximately perpendicular to said plane tangent to the center of the cornea; and a knife assembly connected to said pivot point of the linkage assembly and extending to the side of the eye opposite the arms of the fixation assembly, said knife assembly comprising a knife blade holder adapted for manual manipulation, a knife blade removably carried by said knife holder, and a cutting edge carried at one end of said knife blade for making an incision in the eye, said knife assembly being pivotable about the pivot point on said linkage assembly so that said knife holder may be moved through an arc of a circle by the other hand of said surgeon and so that said cutting edge will penetrate the eye and describe an incision in the form of an arc of a circle when sufficient hand pressure is applied thereto, the operative field being substantially unobstructed by the surgical instrument when the field is viewed from above.

2. The surgical instrument according to claim 1 further comprising a guard slidably mounted on said knife blade for limiting the depth of insertion of said cutting edge into the eye.

3. The surgical instrument according to claim 1 wherein each of said prongs is 2 mm in length.

4. The surgical instrument according to claim 1 wherein said linkage assembly is dimensioned so that said knife blade cutting edge may be positioned in the area of the limbus of the human eye in order to describe an incision extending approximately 180° about the cornea when said knife assembly is caused to pivot about said pivot point.

5. The surgical instrument according to claim 1 wherein said linkage assembly is pivotally connected to said fixation assembly to provide fine adjustment for positioning the knife blade cutting edge in the area of the limbus of the human eye in order to describe an incision extending approximately 180° about the cornea when said knife assembly is caused to pivot about said pivot point.

6. The surgical instrument according to claim 5 wherein said linkage assembly comprises a piston connected to one of said elongated arms of said fixation assembly and extending toward the other of said elongated arms, a cylinder connected to the other of said arms of said fixation device for carrying therein said piston so as to damp the movement of said elongated arms of said fixation assembly toward and away from each other; a first linkage arm supported at one end thereof on said cylinder for adjustable pivotal movement thereabout, means carried by said first linkage arm for preventing pivotal movement thereof about said cylinder so as to adjust the position of said first linkage arm on said cylinder, a coupling member pivotally carried at the other end of said first linkage arm for pivotal movement in a first plane so as to vary the angle of said coupling member with respect to the longitudinal axis of said first linkage arm, a second linkage arm connected at one end thereof to said coupling member at a pivot point for pivotal movement thereabout in a second plane, said knife assembly being carried at the other end of said second linkage arm so that said knife blade and cutting edge may be pivoted about said pivot point by pivotal movement of said second linkage arm thereabout.

7. The surgical instrument according to claim 6 wherein said knife holder is pivotally connected to said other end of said linkage arm so that the angle of said knife blade carried therein may be varied with respect to a plane tangent to the point of contact of said cutting edge with said eye.

8. The surgical instrument according to claim 7 wherein said first linkage arm is provided with abutment shoulders and said coupling member is provided with cooperating abutment surfaces so that the maximum angle therebetween is 180°.

9. The surgical instrument according to claim 5 wherein said linkage assembly comprises first and second "L" shaped linkage arms, each said arm having first and second legs, the distal end of said first leg of each arm being pivotally connected to one of said elongated arms of said fixation assembly, the distal end of the second leg of each of said "L" shaped arms being pivotally connected together defining said pivot point, and a third linkage arm pivotally connected at one end thereof to said second leg of said first and second linkage arms at said pivot point, said knife assembly being carried at the other end of said third linkage arm so that said knife blade and cutting edge may be pivoted about said pivot point by pivotal movement of said third linkage arm thereabout.

10. The surgical instrument according to claim 9 wherein said knife blade holder is connected to said other end of said third linkage arm at an angle to the plane thereof such that said knife blade carried therein will be positioned at a 90° angle with respect to a plane tangent to the point of contact of said cutting edge with said eye so that said cutting edge will form a perpendicular incision.

11. The surgical instrument according to claim 9 wherein said knife blade holder is connected to said other end of said third linkage arm at an angle to the plane thereof such that said knife blade carried therein will be positioned at an angle other than 90° with respect to a plane tangent to the point of contact of said cutting edge with said eye so that said cutting edge will form an incision beveled at an angle directed toward the center of the cornea of the eye.

12. The surgical instrument according to claim 9 wherein said knife blade holder is adjustably connected to said other end of said third linkage arm so that the angle of said knife blade carried therein may be varied with respect to a plane tangent to the point of contact of said cutting edge with said eye.

13. The surgical instrument according to claim 9 further comprising abutment means carried on each of the arms of said fixation assembly so as to prevent axial movement of said "L" shaped linkage arms therealong.

14. The surgical instrument according to claim 1 wherein said knife blade assembly is movably mounted on said linkage assembly for adjustment toward and away from said pivot point.

15. The surgical instrument according to claim 1 wherein said linkage assembly comprises at least one linkage arm being connected at one end thereof to one of said arms of said fixation assembly, the other end of said linkage arm defining said pivot point, said knife assembly being carried at said other end of said linkage arm so that said knife blade and cutting edge may be pivoted about said pivot point.

16. The surgical instrument according to claim 15 wherein said knife blade holder is adjustably connected to said other end of said linkage arm so that the angle of said knife blade carried therein may be varied with respect to a plane tangent to the point of contact of said cutting edge with said eye.

17. The surgical instrument according to claim 1 wherein said linkage assembly is connected to said fixation device for pivotal movement with respect thereto.

18. The surgical instrument according to claim 1 wherein said means for adjusting the radial distance of said knife blade from said pivot point comprises flange means connected to said knife blade holder having a plurality of spaced apart apertures, and a removable pin carried by said linkage assembly at said pivot point, said flange being pivotally supported at said pivot point by said pin engaging one of said apertures.

19. The surgical instrument according to claim 1 wherein said knife blade assembly is mounted for sliding adjustment on said linkage assembly for varying the radial distance of said knife blade from said pivot point.

* * * * *